United States Patent [19]

Okuda et al.

[11] Patent Number: 4,846,801
[45] Date of Patent: Jul. 11, 1989

[54] DRUG DELIVERY DEVICE

[75] Inventors: Kiyoshi Okuda, Ohtsu; Kiyonori Okada; Kazumi Ohtomo; Keiko Nakata, all of Osaka, Japan

[73] Assignee: Fujisawa Pharmaceutical Co., Ltd., Osaka, Japan

[21] Appl. No.: 218,530

[22] Filed: Jul. 14, 1988

Related U.S. Application Data

[63] Continuation of Ser. No. 91,780, Sep. 1, 1987, abandoned.

[30] Foreign Application Priority Data

Sep. 16, 1986 [JP] Japan ............................ 61-142448[U]

[51] Int. Cl.$^4$ .......................................... A61M 5/315
[52] U.S. Cl. .................................. 604/218; 604/275; 604/263
[58] Field of Search ............... 604/218, 192, 263, 187, 604/239, 264, 265, 275, 279, 193

[56] References Cited

U.S. PATENT DOCUMENTS

| 47,248 | 4/1965 | Wheelock | 604/275 X |
| 3,486,503 | 12/1969 | Porter et al. | 604/275 |
| 3,738,539 | 6/1973 | Beich | 604/218 |
| 3,823,715 | 7/1974 | Holanek et al. | 604/218 X |

Primary Examiner—John D. Yasko
Attorney, Agent, or Firm—Oblon, Spivak, McClelland, Maier & Neustadt

[57] ABSTRACT

A drug delivery device includes a cylinder having a large diameter and a drug delivery member coaxially fitted to one end of the cylinder and in fluid communication therewith, the drug delivery member having a diameter substantially smaller than that of the cylinder. Drug delivery orifices are formed only at a side wall of the drug delivery member at an end thereof opposite the cylinder. A plunger fittable into an end of the cylinder opposite the drug delivery member has a disc portion and a central projection which fits into the drug delivery member. A cap covering the drug delivery member has an annular projection on the inside thereof for sealing the drug delivery member.

1 Claim, 2 Drawing Sheets

DRUG DELIVERY DEVICE

This application is a continuation of application Ser. No. 091,780 filed on Sept. 1, 1987, now abandoned.

BACKGROUND OF THE INVENTION

1. Industrial Field of Utilization

This invention relates to a drug delivery device for administration of a fluid medicament such as a gel-form medicament into a cavity of the body, which is used in the field of health care.

2. Prior Art

As a device for delivering a drug into a cavity of the body, such as the rectum, an enemator has been in use for many years. As an improved version of the enemator, there is known a drug delivery device comprising a cylinder having a head portion forming a drug delivery member adapted to be inserted into a cavity of the body, a plunger slidable within said cylinder, and a cap adapted to cover said drug delivery member, said cap being securely abutted at its top against the back of said plunger so as to function as a piston in use of the device (Japanese Design Registration No. 669,474).

PROBLEMS THAT THE INVENTION IS TO SOLVE

With the hitherto-known drug delivery device of the described type, it was inevitable that at completion of delivery of a drug, that is the time when the tip of the plunger abuts the inner wall of the head portion of the cylinder, there still remains some of the drug within the drug delivery means. Since such a drug delivery device is so designed, in consideration of the viscosity and other properties of the drug to be delivered, that its drug delivery means is by far larger than the injection syringe in inside diameter, the residual amount of the drug retained in this portion is substantial. This failure to utilize a drug fully means a substantial economic loss when the drug is an expensive one or the amount for use is small.

To overcome this disadvantage, the present inventors previously developed a drug delivery device such that a projection having a tapered outer circumferential wall advances into a drug delivery member so as to reduce the residual amount of the drug (Japanese Utility Model Application No. 33426/1986) but this device has proved to have room for further improvements.

Thus, the insertion of the drug delivery member into the cavity of the body such as the anus is not as smooth as desired and when its piston was pushed with a sudden force, the drug was not retained at the site of administration but was propelled too deep into the cavity of the body.

SUMMARY OF THE INVENTION

Having been accomplished to overcome the above disadvantages, this invention comprises a drug delivery device comprising a cylinder having a head portion forming a drug delivery member for delivering a drug into a cavity of the body, a plunger slidable within said cylinder and having a front projection adapted to advance into said drug delivery member, and a cap adapted to cover said drug delivery member, characterized in that said drug delivery member is provided with drug delivery orifices in its side wall towards its front end and said cap is provided with an annular projection on its inner side wall, said annular projection being adapted to sealingly engage the outer side wall of said drug delivery member.

DETAILED DESCRIPTION OF THE PREFERRED EMBODIMENTS

An embodiment of this invention will be described in detail hereinafter with reference to the accompanying drawings. It should be understood that, in this specification, the upward direction and the downward direction as viewed in FIG. 1 will be referred to as front and rear, respectively.

Figure 1:
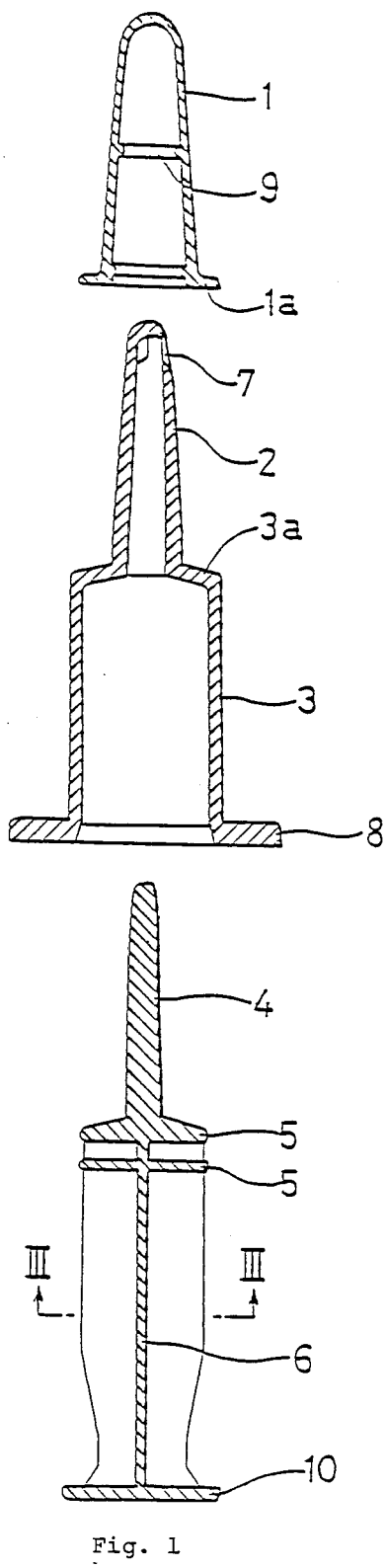
FIG. 1 is a longitudinal section view of the invention prior to assembly.

FIG. 1 is a longitudinal section view showing a drug delivery device according to this invention prior to assembly. The device comprises a cap 1, a cylinder 3 having a drug delivery member 2, and a plunger 5 having a front central projection 4 adapted to fit into said delivery member 2 and having a piston 6 disposed in a rear portion thereof.

Figure 2:
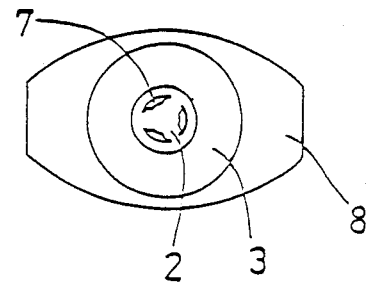
FIG. 2 is a plan view showing the delivery member and cylinder.

The drug delivery member 2 is formed by one-piece molding with the cylinder 3 at its head. The drug delivery member 2 is tapered towards its front end and, as shown in FIG. 2, the side wall thereof is provided with three drug delivery orifices 7. The base of the cylinder 3 is provided with a finger-rest 8 on which fingers can be set in using the device.

The cap 1 is so designed that when it is positioned over the delivery member 2 and a collar 1a formed at its base abuts a shoulder 3a of the cylinder 3, an annular projection 9 formed in the center of the side wall of the cap 1 comes into sealing contact with the outer side wall of the delivery member 2.

Figure 3:
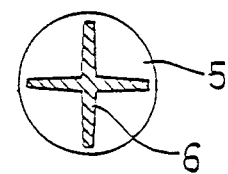
FIG. 3 is a transverse section view taken along the line III—III of FIG. 1.

The plunger 5 comprises a couple of disks and when the front face of the plunger 5 abuts the inner wall of the shoulder 3a of said cylinder, the projection 4 formed centrally in the front of the plunger 5 occupies substantially the whole cavity within the delivery member 2. Further, as illustrated in FIG. 3, a piston 6 having a cruciform section is one-piece molded with the plunger 5 at its back and a finger-rest 10 on which fingers may be set in using the device is one-piece molded with the rear end of the piston 6.

An exemplary mode of use of the above drug delivery device is described hereinafter.

First, the cap 1 is loosely set over the drug delivery member 2 and a predetermined amount of a gel-form medicament M is filled into the delivery member 2 and cylinder 3. Then, the plunger 5 is advanced into the medicament M in the cylinder 3 until the plunger has reached the rear end of the cylinder 3. Thereupon, a portion of the medicament M oozes out from the delivery orifices 7 but it is retained in a space R defined by the inner side wall of the cap 1 and the outer side wall of the delivery member 2 forwardly of the annular projection 9 of the cap 1. Then, as the cap 1 is tightened until the collar 1a of the cap 1 abuts the outer wall of the shoulder 3a of the cylinder, the annular projection 9 comes into sealing contact with the outer side wall of the delivery member and the medicament M oozing out from the delivery orifices 7 spread evenly into the space R.

Figure 4:
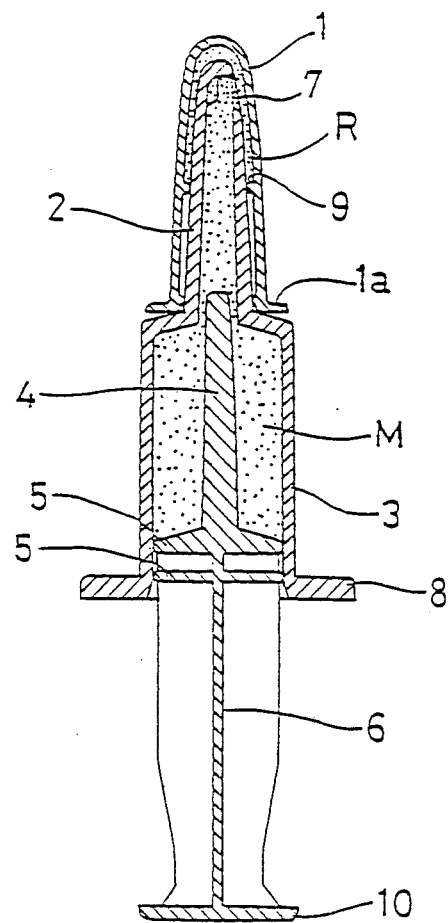
FIG. 4 is a longitudinal section view showing the device filled with a drug.

The drug delivery device thus filled with the medicament M (FIG. 4) is preferably sealed tight, for example by shrink packaging.

To administer the drug, the drug delivery member 2 is inserted into the cavity of the body such as the anus and, then, the finger-rest 10 is pressed forward just as in the case of the ordinary drug delivery device, whereby the medicament M is delivered into the cavity of the body from the delivery orifices 7.

It should be understood that the above is only one embodiment of the invention and that many changes and modifications may be made by those skilled in the art without departing from the scope of this invention.

For example, the size of the cylinder may be freely selected in view of the amount of a medicament to be filled therein and the length and shape of the delivery member may be fitted to the body cavity into which the device is inserted. The number of drug delivery orifices is optional and the piston may be rod-shaped. The drug delivery member may be a cylindrical member without a taper and the projection to be advanced into it may likewise be a columnar member with a diameter slightly smaller than the inner diameter of the cylindrical member, so long as the medicament M is able to enter the drug delivery member from the cylinder 3. Furthermore, as shown in Japanese Design Registration No. 669,474, it may be so arranged that the cap is affixed to the rear wall of the plunger so as to serve as a piston.

Effects

As the drug delivery device according to this invention is such that drug delivery orifices are formed in the side wall towards the tip of a drug delivery member, the drug is not propelled too far into the cavity of the body but retained in the cavity at the site of administration even if the piston is pushed with a force in use, so that the efficacy of the drug may be assured with certainty.

Moreover, this device can be easily inserted into a cavity of the body because the drug delivery end is smoothened by the drug retained between the outer wall of the delivery member and the inner wall of the cap forwardly of the annular projection provided on the inner side wall of the cap.

What we claim is:

1. A drug delivery device comprising:
   a cylinder having a large diameter;
   a drug delivery member comprising a hollow elongate element coaxially fitted to one end of said cylinder and in fluid communication therewith so as to form a head portion for delivering a drug, said drug delivery member having a diameter substantially smaller than that of said cylinder and being filled with a drug;
   drug delivery orifices only in a side wall of said hollow elongate element at an end thereof opposite said cylinder;
   a plunger fittable into an end of said cylinder opposite said drug delivery member, said plunger having a disc portion comprising means for advancing a drug in said cylinder towards said drug delivery member as said plunger is advanced toward said drug delivery member, said plunger also having a central projection which fits into said drug delivery member when said plunger is advanced, said central projection and drug delivery member being shaped such that a drug in said hollow cylinder is permitted to flow into said drug delivery member when said central projection is fitted into said drug delivery member as said plunger is advanced; and
   a cap shaped to cover said drug delivery member, said cap having an annular projection on an inner side wall thereof, said annular projection sealingly engaging the side wall of said hollow elongate element when said cap is fitted on said drug delivery member to define an annular space evenly filled with said drug, said cap comprising means for leaving said orifices open when said cap is fitted on said drug delivery member, whereby said drug may be caused to fill said annular space by advancing said plunger while said cap is fitted on said drug delivery member.

* * * * *